United States Patent
Sabczynski et al.

(10) Patent No.: US 11,389,245 B2
(45) Date of Patent: Jul. 19, 2022

(54) TRANSFORMATION DETERMINATION FOR ANATOMICALLY ALIGNING FRAGMENTS OF A BROKEN BONE

(71) Applicant: KONINKLIJKE PHILIPS N.V., Eindhoven (NL)

(72) Inventors: Joerg Sabczynski, Norderstedt (DE); Christian Buerger, Hamburg (DE); Michael Grass, Buchholz in der Nordheide (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/619,954

(22) PCT Filed: Jun. 26, 2018

(86) PCT No.: PCT/EP2018/067012
§ 371 (c)(1),
(2) Date: Dec. 6, 2019

(87) PCT Pub. No.: WO2019/002234
PCT Pub. Date: Jan. 3, 2019

(65) Prior Publication Data
US 2021/0077191 A1   Mar. 18, 2021

(30) Foreign Application Priority Data
Jun. 30, 2017 (EP) .................... 17179058

(51) Int. Cl.
*G06T 15/00* (2011.01)
*A61B 34/10* (2016.01)
(Continued)

(52) U.S. Cl.
CPC ............. *A61B 34/10* (2016.02); *G06T 7/0012* (2013.01); *G06T 7/11* (2017.01); *G06T 17/20* (2013.01);
(Continued)

(58) Field of Classification Search
CPC ......... G06T 19/00; G06T 17/20; G06T 17/00; G06T 15/10; G06T 15/00
(Continued)

(56) References Cited

U.S. PATENT DOCUMENTS

2009/0281420 A1* 11/2009 Passmore ................ G06T 7/254
  600/425
2014/0278322 A1* 9/2014 Jaramaz ................ G16H 50/50
  703/11
(Continued)

FOREIGN PATENT DOCUMENTS

WO   2016/007936   1/2015

OTHER PUBLICATIONS

International Search Report and Written Opinion dated Oct. 22, 2018 for International Application No. PCT/EP2018/067012 Filed Jun. 26, 2018.
(Continued)

*Primary Examiner* — Gordon G Liu

(57) ABSTRACT

There is provided a computer-implemented method (200) and apparatus for determining a transformation for anatomically aligning fragments of a broken bone. An image of the broken bone of the subject is acquired (202). The bone is broken into two or more fragments. A model of a corresponding unbroken bone and at least one parameter is acquired. The at least one parameter defines one or more deformations to the model that are permitted when fitting portions of the model of the unbroken bone to corresponding fragments of the broken bone (204). Portions of the model
(Continued)

of the unbroken bone are fit to corresponding fragments of the broken bone based on the at least one parameter (206). A transformation is determined that anatomically aligns the fragments of the broken bone with the corresponding portions of the model (208).

20 Claims, 4 Drawing Sheets

(51) Int. Cl.
  *G06T 7/11* (2017.01)
  *G06T 7/00* (2017.01)
  *G06T 17/20* (2006.01)
  *G06T 19/20* (2011.01)
  *A61B 17/56* (2006.01)

(52) U.S. Cl.
  CPC ........ *G06T 19/20* (2013.01); *A61B 2017/564* (2013.01); *A61B 2034/105* (2016.02); *G06T 2207/10081* (2013.01); *G06T 2207/30008* (2013.01); *G06T 2219/2004* (2013.01); *G06T 2219/2016* (2013.01)

(58) Field of Classification Search
  USPC .......................................................... 345/419
  See application file for complete search history.

(56) References Cited

U.S. PATENT DOCUMENTS

2016/0331463 A1* 11/2016 Notzli ..................... G06T 17/00
2017/0367766 A1* 12/2017 Mahfouz ............ A61B 17/1703

OTHER PUBLICATIONS

Albrecht, et al; "Automatic Fracture Reduction" In: Joshua A. Levine et al: "Mesh Processing in Medical Image Analysis 2012", Oct. 1, 2012.

Gong, et al: "Reduction of multi-fragment fractures of the distal radius using atlas-based 2D/3D registration", Spie Proceedings, vol. 7261, 726137, Mar. 13, 2009.

Jiménez-Delgado, et al: "Computer assisted preoperative planning of bone fracture reduction: Simulation techniques and new trends", Medical Image Analysis, vol. 30, May 31, 2016.

Buschbaum, et al: "Computer-assisted fracture reduction: a new approach for repositioning femoral fractures and planning reduction paths", Int J Cars (2015) 10:149-159.

Furnstahl, et al: "Computer assisted reconstruction of complex proximal humerus fractures for preoperative planning", Medical Image Analysis 16 (2012) 704 720.

Ron, et al: "Computer-Based Periaxial Rotation Measurement for Aligning Fractured Femur Fragments from CT: A Feasibility Study", Computer Aided Surgery 7:332-341 (2002).

Troulis, et al: "Development of a three-dimensional treatment planning system based on computed tomographic data", Int. J. Oral Maxillofac. Surg. 2002; 31: 349-357.

\* cited by examiner

TRANSFORMATION DETERMINATION FOR ANATOMICALLY ALIGNING FRAGMENTS OF A BROKEN BONE

CROSS REFERENCE TO RELATED APPLICATIONS

This application is the U.S. National Phase application under 35 U.S.C. § 371 of International Application No. PCT/EP2018/067012 filed Jun. 26, 2018, published as WO 2019/002234 on Jan. 3, 2019, which claims the benefit of European Patent Application Number 17179058.7 filed Jun. 30, 2017. These applications are hereby incorporated by reference herein.

TECHNICAL FIELD OF THE INVENTION

This disclosure relates to the field of image processing and, in particular, to a method and apparatus for determining a transformation for anatomically aligning fragments of a broken bone.

BACKGROUND TO THE INVENTION

Treatment of complex fractures (for example, of the humerus, femur or tibia) can be complicated especially in elderly patients. Several different techniques for fixation of complex fractures are available, such as intramedullary devices, plates and screws, or external fixation. The first step in the operative procedure is fracture reduction, i.e. moving bone fragments into the correct position, either in an open approach (such as open reduction and internal fixation, ORIF) or a minimally invasive approach (such as minimally invasive plate osteosynthesis, MIPO), before full fixation can be completed.

Before performing fracture reduction, the surgeon must determine how to correctly align the bone fragments, and this requires detailed planning in order to assemble the fragments in the optimal way. Medical images, such as x-ray or computed tomography (CT) images, can provide an indication of the number of bone fragments that need to be re-assembled and their positions. Surgeons can also make use of virtual planning tools that enable them to view and move portions of an image of the bone to determine the manner in which the bone fragments need to be moved to reassemble or reconstruct the bone. However, such tools often require a substantial amount of user interaction on a computer screen. This user interaction can be tedious and prone to errors.

In some existing tools, a surgeon may be supported by a computer program that fits a model to the fragments of a broken bone. However the accuracy of such tools is hampered by the accuracy of the models used. In particular, some tools assume that the body is symmetrical and thus, for example, use a reflection of a model of an unbroken bone in the left leg to reconstruct an equivalent broken bone in the right leg.

These methods have the drawback that the body is not necessarily symmetrical and thus the method can produce unreliable results. Furthermore, the methods cannot be used when planning the reconstruction of a bone for which there is no equivalent symmetrical bone. Moreover, as the model used for the reconstruction may not properly represent the bone that is to be reconstructed, the reconstruction will be of a poor quality and can risk the health of the patent if followed in practice.

An automated fracture reduction technique to reposition fractured bones in their correct anatomical alignment is disclosed in "Computer-assisted fracture reduction: a new approach for repositioning femoral fractures and planning reduction paths", by Jan Buschbaum et al, Int J CARS (2015) 10:149-159. In the disclosed technique, the bone fragments are segmented from a CT scan and virtual three-dimensional (3D) models are created. The technique extracts fracture lines based on computed surface curvatures of the models and, by using surface properties, the fracture edges are then reconstructed and the fragments repositioned. However, this technique is prone to errors and thus also produces unreliable results, because the method assumes that there must be a fracture where the curvature is highest. This can result in errors being propagated through the method if the initial segmentation is not of high enough accuracy.

"Automatic Fracture Reduction" by Albrecht et al., MeshMed 2012, LNCS vol. 7599, pp. 22-29, 2012, describes a method to automatically reposition the fragments of a broken bone based on surface meshes segmented from CT scans.

"Reduction of Multi-Fragment Fractures of the Distal Radius Using Atlas-based 2D/3D Registration" by Gong et al., Medical Imaging 2009, Proc. of SPIE Vol 7261, describes a method of fitting a distal radius atlas with changing shape to a set of co-registered interoperative X-ray images.

There is however a need for an improved method and apparatus for determining a transformation for anatomically aligning fragments of a broken bone.

SUMMARY OF THE INVENTION

As noted above, a limitation with existing approaches is that the approaches are prone to errors and thus produce unreliable information for planning the realignment or reconstruction of a broken bone of a subject, which can have a detrimental effect on the subject if followed in practice. It is therefore desirable to provide an improved method and apparatus for determining a transformation for anatomically aligning fragments of a broken bone.

Therefore, according to a first aspect, there is provided a computer-implemented method for determining a transformation for anatomically aligning fragments of a broken bone. The method comprises acquiring an image of a broken bone of a subject, wherein the bone is broken into two or more fragments. The method also comprises acquiring a model of a corresponding unbroken bone and at least one parameter defining one or more deformations to the model that are permitted when fitting portions of the model of the unbroken bone to corresponding fragments of the broken bone, fitting portions of the model of the unbroken bone to corresponding fragments of the broken bone based on the at least one parameter, and determining a transformation that anatomically aligns the fragments of the broken bone with the corresponding portions of the model.

In particular, a 3D image of a broken bone of a subject may be acquired. The model may be a 3D mesh model. The model may be divided into portions that correspond to the fragments of the broken bone. The portions may be fitted to corresponding fragments of the broken bone in the 3D image. Said fitting may comprise adjusting the portions of the model of the unbroken bone. Said adjusting may be restricted to the one or more deformations defined by the parameter(s). Based on said fitted portions of the model, a transformation may be determined that anatomically aligns the fragments of the broken bone with the corresponding portions of the undivided model of the unbroken bone.

In some embodiments, the model of the corresponding unbroken bone may comprise a mesh derived from one or more corresponding unbroken bones of other subjects. For example, the mesh may be a surface mesh or a volume mesh, e.g., a tetrahedral mesh.

In some embodiments, fitting portions of the model of the unbroken bone to corresponding fragments of the broken bone may comprise adjusting the model according to the at least one parameter to fit the portions of the model of the unbroken bone to the corresponding fragments of the broken bone.

In some embodiments, at least one parameter may define any one or more of: one or more directions in which the model is adjustable, one or more dimensions within which the model is adjustable, an upper limit on the extent to which the position of a portion of the model is adjustable with respect to a position of another portion of the model, and an upper limit on the extent to which the position of a portion of the model is adjustable with respect to another portion of the model. In some embodiments, the at least one parameter may relate to a parameter space of permitted deformations to different parts of the model.

In some embodiments, the method may further comprise acquiring an attribute of the subject and fitting portions of the model of the unbroken bone to corresponding fragments of the broken bone may comprise restricting the parameter space of permitted deformations to deformations corresponding to shapes of unbroken bones that are consistent with the acquired attribute of the subject. For example, if the model is a volume mesh, the attribute may be a size of the volume of all bone fragments in the image data. The parameter space of permitted deformations may be restricted so that the volume of all volume mesh parts fitted to the image data corresponds to said volume.

In some embodiments, the method may further comprise determining information about the fragments of the broken bone of the subject and adjusting the determined transformation based on the information, to anatomically align the fragments of the broken bone. In some embodiments, the information determined about the fragments of the broken bone of the subject may comprise information indicative of density variations in the fragments. In some embodiments, the information determined from the fragments of the broken bone of the subject may comprise information indicative of a location of one or more trabecular structures in the fragments of the broken bone, and adjusting may comprise adjusting the determined transformation based on the information indicative of the location of the one or more trabecular structures, to anatomically align the one or more trabecular structures. In some embodiments, the location of the one or more trabecular structures may be acquired from density variations in the fragments.

In some embodiments, fitting may comprise dividing the model into the portions that correspond to the fragments of the broken bone. In some embodiments, dividing may comprise, for one or more of the fragments of the broken bone, identifying a surface of the fragment that has broken away from at least one other fragment and dividing the model along a corresponding surface in the model.

In some embodiments, the model may be a statistical shape model and the at least one parameter may comprise at least one eigenmode of the statistical shape model.

According to a second aspect, there is provided a computer program product comprising a computer readable medium, the computer readable medium having computer readable code embodied therein, the computer readable code being configured such that, on execution by a suitable computer or processor, the computer or processor is caused to perform the method as described above.

According to a third aspect, there is provided an apparatus for determining a transformation for anatomically aligning fragments of a broken bone. The apparatus comprises a processor configured to acquire an image of a broken bone of a subject, wherein the bone is broken into two or more fragments. The processor is also configured to acquire a model of a corresponding unbroken bone and at least one parameter defining one or more deformations to the model that are permitted when fitting portions of the model of the unbroken bone to corresponding fragments of the broken bone, fit portions of the model of the unbroken bone to corresponding fragments of the broken bone based on the at least one parameter and determine a transformation that anatomically aligns the fragments of the broken bone with the corresponding portions of the model.

According to the aspects and embodiments described above, the limitations of existing techniques are addressed. In particular, according to the above-described aspects and embodiments, a model of a corresponding unbroken bone and at least one parameter describing one or more deformations to the model that are permitted when fitting corresponding portions of the model of the unbroken bone to the fragments of the broken bone are acquired. As such, deformations of the model according to the at least one parameter are allowed when the corresponding portions of the model of the unbroken bone are fitted to the fragments of the broken bone. This can ensure that the model that is used to determine the transformation accurately reflects (for example, the shape) of the bone in the image. This provides a more accurate fit, compared to assuming a fixed model, and thus the determined transformation that anatomically aligns the fragments of broken bone is more reliable.

There is thus provided an improved method and apparatus for determining a transformation for anatomically aligning fragments of a broken bone, which overcomes the existing problems.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

As noted above, there is provided an improved method and apparatus for determining a transformation for anatomically aligning fragments of a broken bone, which overcomes the existing problems.

Figure 1:
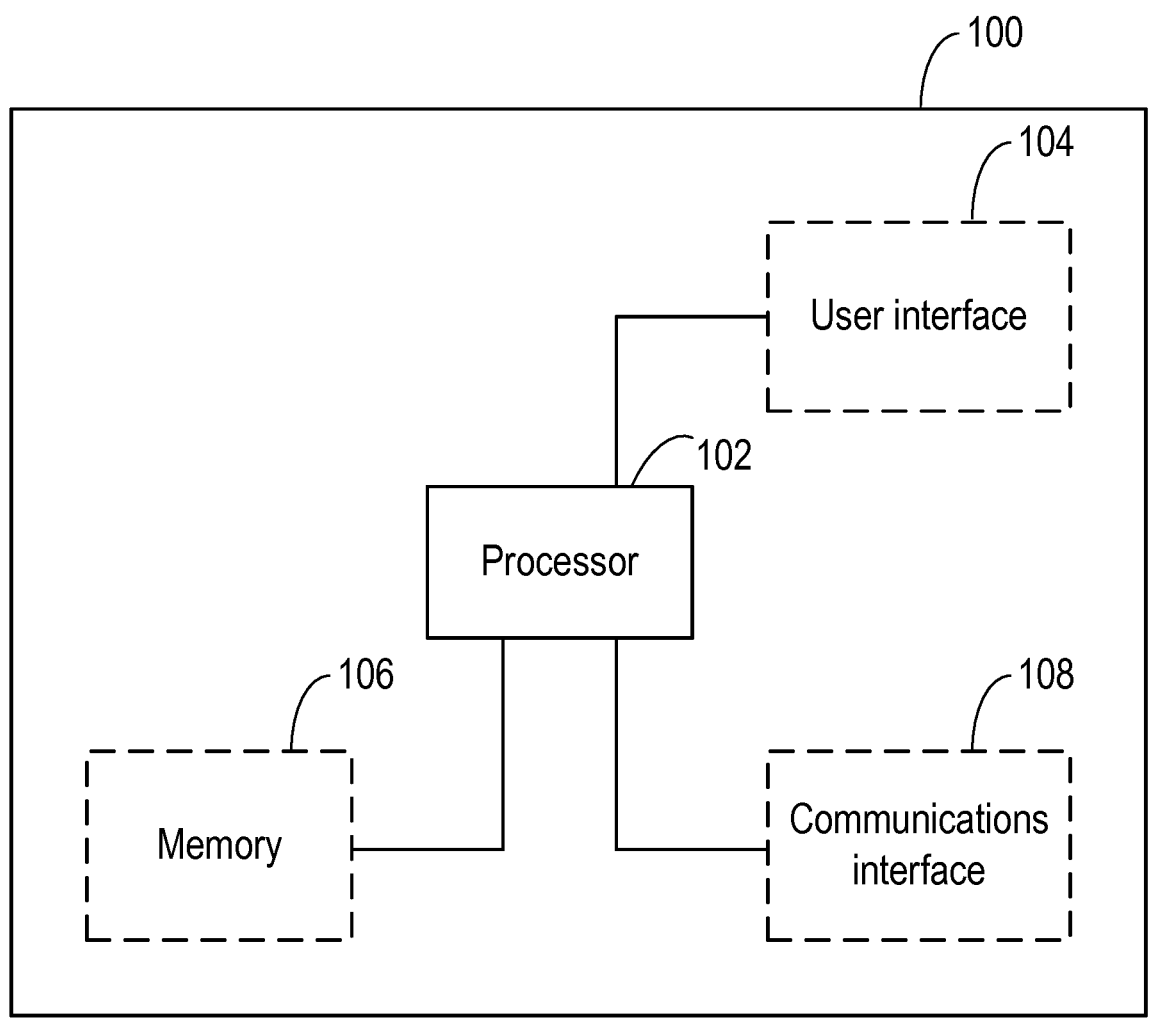
FIG. 1 is a block diagram of an apparatus for determining a transformation for anatomically aligning fragments of a broken bone according to an embodiment.

FIG. 1 shows a block diagram of an apparatus 100 according to an embodiment that can be used for determining a transformation for anatomically aligning fragments of a broken bone. With reference to FIG. 1, the apparatus 100 comprises a processor 102 that controls the operation of the apparatus 100 and that can implement the method described herein. The processor 102 can comprise one or more processors, processing units, multi-core processors or modules that are configured or programmed to control the apparatus 100 in the manner described herein. In particular implementations, the processor 102 can comprise a plurality of software and/or hardware modules that are each configured to perform, or are for performing, individual or multiple steps of the method described herein.

Briefly, the processor 102 of the apparatus 100 is configured to acquire an image of a broken bone of a subject, wherein the bone is broken into two or more fragments, and is also configured to acquire a model of a corresponding unbroken bone and at least one parameter defining one or more deformations to the model that are permitted when fitting portions of the model of the unbroken bone to corresponding fragments of the broken bone. The processor 102 is further configured to fit portions of the model of the unbroken bone to corresponding fragments of the broken bone based on the at least one parameter and determine a transformation that anatomically aligns the fragments of the broken bone with the corresponding portions of the model.

In any of the embodiments described herein, the image can be a two-dimensional image, a three-dimensional image, or any other dimensional image. The image can, for example, be a medical image, or any other type of image, of a broken bone. Examples of a medical image include, but are not limited to, a computed tomography (CT) image (for example, from a CT scan) such as a C-arm CT image, a spectral CT image or a phase contrast CT Image, an x-ray image (for example, from an x-ray scan), a magnetic resonance (MR) image (for example, from an MR scan), or any other medical image of a broken bone. Although examples have been provided for the type of image, a person skilled in the art will appreciate that the teachings provided herein may equally be applied to any other type of image in which a broken bone is present.

As mentioned earlier, the broken bone of the subject in the image is broken into two or more (i.e. a plurality of) fragments. Thus, the image at least comprises two or more different fragments of the broken bone. However, it will be appreciated that the image may not necessarily comprise the entire bone and may, for example, only comprise the portion of the broken bone that contains the break. The bone in the image can be any bone, such as a femur, a tibia, an ulna, a radius, a rib, or any other bone, or any combination of bones.

As mentioned earlier, a model of a corresponding unbroken bone is acquired for use by the processor 102. The model of the corresponding unbroken bone can be a two-dimensional model of the corresponding unbroken bone, a three-dimensional model of the corresponding unbroken bone, or any other dimensional model of the corresponding unbroken bone. It will be understood that the unbroken bone is corresponding in that it is a model of the same type of bone as the bone in the image. For example, if the broken bone in the image is a left femur, the model of a corresponding unbroken bone is a model of an unbroken left femur. In other words, the unbroken bone is corresponding in that it represents the broken bone in an unbroken form. Although examples have been provided for the type of bone in the image and model, it will be understood that the image may comprise any type of bone that is broken into two or more fragments and the model may comprise any type of bone that corresponds to the bone in the image.

In some embodiments, as illustrated in FIG. 1, the apparatus 100 may comprise at least one user interface 104. Alternatively or in addition, at least one user interface 104 may be external to (i.e. separate to or remote from) the apparatus 100. For example, at least one user interface 104 may be part of another device. A user interface 104 may be for use in providing a user of the apparatus 100 (for example, a medical personnel, a healthcare provider, a healthcare specialist, a care giver, a subject, or any other user) with information resulting from the method according to embodiments herein. The processor 102 may be configured to control one or more user interfaces 104 to provide information resulting from the method according to embodiments herein. For example, the processor 102 may be configured to control one or more user interfaces 104 to render (or output or display) the image of the broken bone, the model of the corresponding unbroken bone, the model of the unbroken bone fitted to the fragments of the broken bone in the image, the determined transformation that anatomically aligns the fragments of the broken bone with the corresponding portions of the model and/or a virtual reconstruction (or reassembly) of the broken bone that shows the determined transformation being applied to the model to rearrange (or re-assemble) the fragments of the broken bone into an unbroken form. Alternatively or in addition, a user interface 104 may be configured to receive a user input. In other words, a user interface 104 may allow a user of the apparatus 100 to manually enter instructions, data, or information. The processor 102 may be configured to acquire the user input from one or more user interfaces 104.

A user interface 104 may be any user interface that enables rendering (or output or display) of information, data or signals to a user of the apparatus 100. Alternatively or in addition, a user interface 104 may be any user interface that enables a user of the apparatus 100 to provide a user input, interact with and/or control the apparatus 100. For example, the user interface 104 may comprise one or more switches, one or more buttons, a keypad, a keyboard, a touch screen or an application (for example, on a tablet or smartphone), a display screen, a graphical user interface (GUI) or other visual rendering component, one or more speakers, one or more microphones or any other audio component, one or more lights, a component for providing tactile feedback (e.g. a vibration function), or any other user interface, or combination of user interfaces.

In some embodiments, as illustrated in FIG. 1, the apparatus 100 may also comprise a memory 106 configured to store program code that can be executed by the processor 102 to perform the method described herein. Alternatively or in addition, one or more memories 106 may be external to (i.e. separate to or remote from) the apparatus 100. For example, one or more memories 106 may be part of another device. A memory 106 can be used to store images, information, data, signals and measurements acquired or made by the processor 102 of the apparatus 100 or from any interfaces, memories or devices that are external to the apparatus 100. The processor 102 may be configured to control the memory 106 to store the images, information, data, signals and measurements. For example, a memory 106 may be used to store the image of the broken bone, the model of the corresponding unbroken bone, the model of the unbroken bone fitted to the fragments of the broken bone in the image, the determined transformation that anatomically aligns the fragments of the broken bone with the corresponding portions of the model and/or a virtual reconstruction (or reassembly) of the broken bone that shows the determined transformation being applied to the model to rearrange (or re-assemble) the fragments of the broken bone into an unbroken form.

In some embodiments, as illustrated in FIG. 1, the apparatus 100 may also comprise a communications interface (or circuitry) 108 for enabling the apparatus 100 to communicate with any interfaces, memories and devices that are internal or external to the apparatus 100. The communications interface 108 may communicate with any interfaces, memories and devices wirelessly or via a wired connection. For example, in an embodiment where one or more user interfaces 104 are external to the apparatus 100, the communications interface 108 may communicate with the one or more external user interfaces 104 wirelessly or via a wired connection. Similarly, in an embodiment where one or more memories 106 are external to the apparatus 100, the communications interface 108 may communicate with the one or more external memories 106 wirelessly or via a wired connection.

It will be appreciated that FIG. 1 only shows the components required to illustrate this aspect of the disclosure and, in a practical implementation, the apparatus 100 may comprise additional components to those shown. For example, the apparatus 100 may comprise a battery or other power supply for powering the apparatus 100 or means for connecting the apparatus 100 to a mains power supply.

Figure 2:
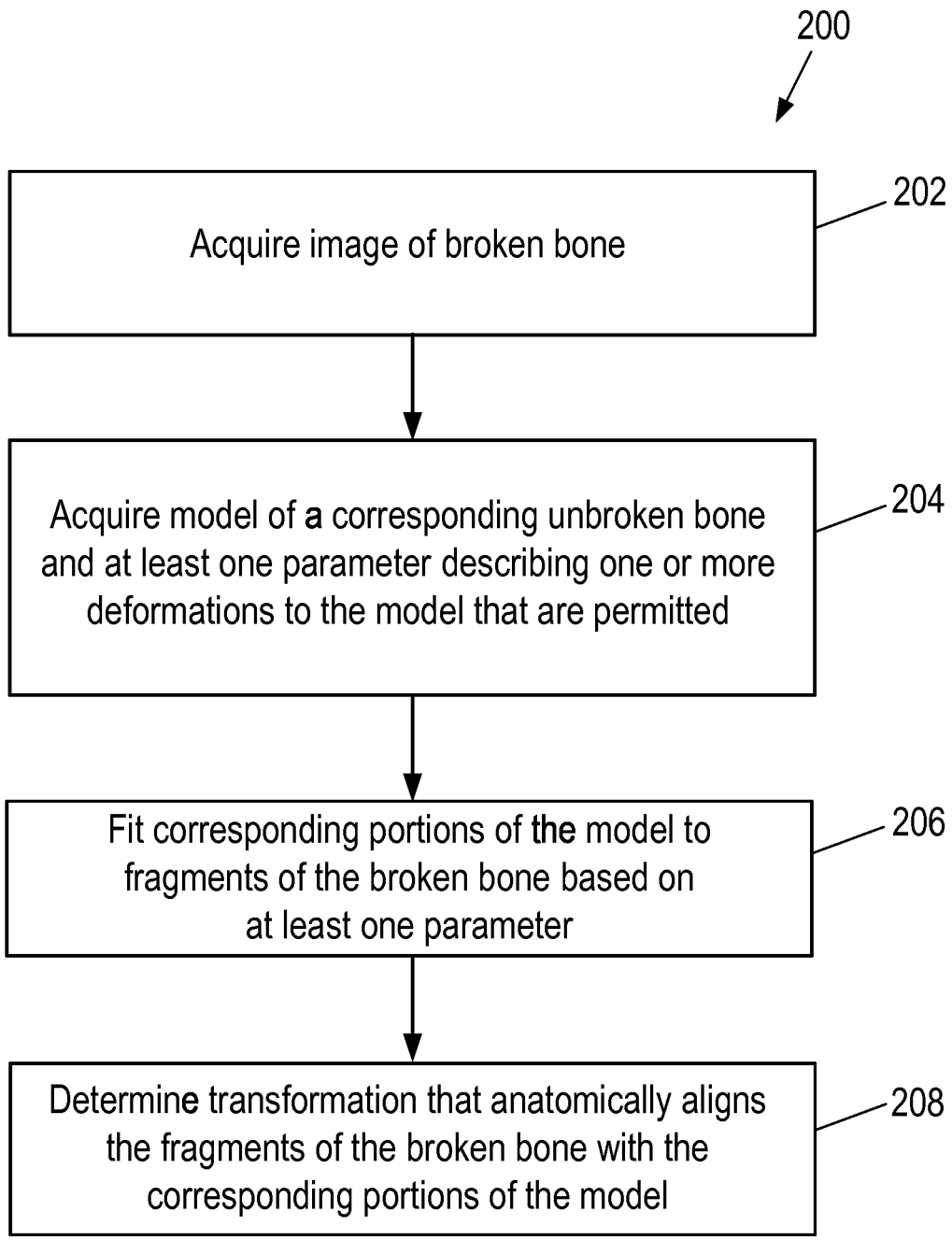
FIG. 2 illustrates a computer-implemented method for determining a transformation for anatomically aligning fragments of a broken bone according to an embodiment.

FIG. 2 illustrates a computer-implemented method 200 for determining a transformation for anatomically aligning fragments of a broken bone. The illustrated method 200 can generally be performed by or under the control of the processor 102 of the apparatus 100. The method may can be partially or fully automated according to some embodiments.

Briefly, with reference to FIG. 2, the method comprises acquiring an image of a broken bone of a subject (at block 202 of FIG. 2), wherein the bone is broken into two or more fragments, and acquiring a model of a corresponding unbroken bone and at least one parameter defining one or more deformations to the model that are permitted when fitting portions of the model of the unbroken bone to corresponding fragments of the broken bone (at block 204 of FIG. 2). The method also comprises fitting portions of the model of the unbroken bone to corresponding fragments of the broken bone based on the at least one parameter (at block 206 of FIG. 2) and determining a transformation that anatomically aligns the fragments of the broken bone with the corresponding portions of the model (at block 208 of FIG. 2).

In more detail, at block 202 of FIG. 2, an image of a broken bone of a subject is acquired, where the bone is broken into two or more fragments. In any of the embodiments disclosed herein, it can be assumed that a total volume of the two or more fragments of the broken bone of the subject is equal to a volume of the unbroken bone of the subject. The processor 102 of the apparatus acquires the image of the broken bone of the subject.

In some embodiments, the processor 102 may acquire the image of the broken bone of the subject from imaging equipment (or medical imaging equipment). For example, in an embodiment where the image is a computed tomography (CT) image, the processor 102 may acquire the CT image of the broken bone of the subject from a CT scanner. Similarly, for example, in an embodiment where the image is an x-ray image, the processor 102 may acquire the x-ray image of the broken bone of the subject from an x-ray machine. In some embodiments, the image of the broken bone of the subject may be stored in a memory (for example, a memory of a database, a server, or any other memory). For example, the processor 102 may download the image of the broken bone of the subject from the memory. The memory 106 may be a memory of the apparatus 100 or a memory that is external to the apparatus 100.

Returning back to FIG. 2, at block 204, a model of a corresponding unbroken bone and at least one parameter defining one or more deformations to the model that are permitted when fitting portions of the model of the unbroken bone to corresponding fragments of the broken bone are acquired. More specifically, the processor 102 of the apparatus acquires the model of the corresponding unbroken bone and the at least one parameter defining one or more permitted deformations to the model.

Generally, the acquired model comprises an indication of the shape of the broken bone in its unbroken form. For example, the acquired model may be shaped according to a generic shape of the unbroken bone. In some embodiments, the acquired model of the unbroken bone is a model that is derived from (or generated based on) one or more corresponding unbroken bones of other subjects. In other words, the acquired model of the unbroken bone may be a model that is derived from (or generated based on) one or more unbroken bones of other subjects that are the same type of bone as the broken bone of the subject in the image. Thus, the acquired model of the unbroken bone may be shaped according to the properties of one or more corresponding unbroken bones of other subjects. For example, the model may be shaped according to an average (or mean) shape of one or more corresponding unbroken bones of other subjects. The other subjects can be a reference population of healthy subjects. The one or more corresponding unbroken bone of other subjects may be representative of a range of bone shapes and/or sizes.

Alternatively or in addition to the one or more corresponding unbroken bones of other subjects, in some embodiments, the model of the unbroken bone may be derived from (or generated based on) medical literature of one or more corresponding unbroken bones, medical research of one or more corresponding unbroken bones, and/or a drawing by a medical professional of one or more corresponding unbroken bones.

In some embodiments, the model of the corresponding unbroken bone can comprise a plurality of adjustable control points, where each control point may correspond to a different point on the surface of the model. The control points are adjustable to deform the model of the corresponding unbroken bone. In some embodiments, the acquired model of the corresponding unbroken bone can comprise a mesh. Thus, in these embodiments, the acquired mesh may be a mesh that is derived from one or more corresponding unbroken bones of other subjects, medical literature, medical research, and/or a drawing by a medical professional. The mesh can comprise a plurality of segments. In some embodiments, the segments can be any shaped polygon and thus the mesh can be any shaped polygon mesh. For example, the segments can be triangular shaped segments and thus the mesh can be a triangular mesh. However, although an example is provided, it will be understood that any other shaped segments are possible and thus any other shaped mesh is also possible. In an example, the model of the corresponding unbroken bone can comprise a surface mesh representing typical anatomical mean shapes of corresponding unbroken bones and optionally also volumetric information such as (for example, spatially encoded) trabecular density and orientation information, which will be explained in more detail later. In another example, the model of the corresponding unbroken bone can comprise a volume mesh, such as a tetrahedral mesh.

As mentioned earlier, in addition to a model of a corresponding unbroken bone being acquired at block 204 of FIG. 2, at least one parameter is also acquired. The at least one acquired parameter defines (or describes or sets) one or more deformations (or adjustments) to the model that are permitted when fitting portions of the model of the unbroken bone to corresponding fragments of the broken bone.

For example, in some embodiments, the at least one parameter can define an upper limit on the extent to which the position of a portion of the model is deformable (or adjustable). Alternatively or in addition, the at least one parameter can define an upper limit on the extent to which the position of a portion of the model is deformable (or adjustable) with respect to another portion of the model. Alternatively or in addition, the at least one parameter can define one or more directions in which the model is deformable (or adjustable). Alternatively or in addition, the at least one parameter can define one or more dimensions within which the model is deformable (or adjustable). In embodiments where the at least one parameter defines an upper limit on the extent, the extent to which the position of a portion of the model is deformable (or adjustable) may be in a certain direction and/or dimension.

Alternatively or in addition to any of the above, the at least one parameter may relate to a parameter space of permitted deformations (or adjustments) to different parts of the model. For example, the at least one parameter may define a range of permitted deformations (or adjustments) to a particular control point of the model in the parameter space or to a particular combination of control points of the model in the parameter space, and/or may define an extent by which one or more control points of the model may be permitted to be deformed in the parameter space, for example, when in a particular mode of deformation. A permitted deformation (or adjustment) to the model may correspond to a positon of one or more control points of the model in the parameter space. Thus, different positions of the one or more control points of the model in the parameter space can correspond to different bone shapes.

According to any of the embodiments described herein, the at least one parameter that defines one or more permitted deformations to the model can, for example, be set according to at least one characteristic of the one or more corresponding unbroken bones. The at least one characteristic may comprise, for example, a range for the size of the one or more corresponding unbroken bones, a general morphology of the one or more corresponding unbroken bones, or any other characteristic, or any combination of characteristics, of the one or more corresponding unbroken bones. For example, the upper limit described earlier may be defined (or set) based on maximum and minimum proportions of the one or more corresponding unbroken bones. The at least one parameter thus ensures that any deformation (or adjustment) that is made to the acquired model in the fitting process, which will be described later, is consistent with the one or more corresponding unbroken bones and is thus reasonable.

In some embodiments, the acquired model of a corresponding unbroken bone can be a statistical shape model. In these embodiments, the at least one parameter may be an eigenmode of one or more control points of the acquired model. The eigenmode of a control point of the acquired model defines a mode of variation (or vibration or movement) permitted to the control point. For example, in some embodiments, the eigenmode of a control point of the acquired model defines the manner in which an adjustment to one or more other control points of the acquired model affects (or constrains) the position of the control point in the acquired model.

Thus, in the manner described above, a model of a corresponding unbroken bone and at least one parameter defining one or more permitted deformations to the model are acquired. Then, returning back to FIG. 2, at block 206, portions of the model of the unbroken bone are fitted to corresponding fragments of the broken bone based on the at least one parameter. More specifically, the processor 102 of the apparatus 100 performs the fitting of portions of the model of the unbroken bone to corresponding fragments of the broken bone.

In some embodiments, the fitting of portions of the model of the unbroken bone to corresponding fragments of the broken bone at block 206 can comprise dividing (or segmenting) the model of the unbroken bone into the portions that correspond to the fragments of the broken bone in the image. In some embodiments, this may be performed by fitting a portion of the model of the unbroken bone to a corresponding fragment of the broken bone in the image and then dividing (or segmenting) the model at the point (or points) at which the fragment is broken from at least one other fragment. This leaves the portion of the model of the unbroken bone fitted to the corresponding fragment of the broken bone and one or more other portions of the model of the unbroken bone, which can then be fitted to the other fragments of the bone. Thus, for one or more of the fragments of the broken bone, a surface of the fragment that has broken from (for example, broken away from) at least one other fragment may be identified and the model of the unbroken bone may be divided (or segmented) along a corresponding surface in the model. As mentioned earlier, one or more remaining portions of the model of the unbroken bone can then be fitted to one or more other fragments of the broken bone in the image. In this way, portions of the model of the unbroken bone can be fitted to different fragments of the broken bone in the image without overlap.

In some embodiments, the fitting of portions of the model of the unbroken bone to corresponding fragments of the broken bone based on the at least one parameter at block 206 of FIG. 2 can comprise adjusting the model according to the at least one parameter to fit the portions of the model of the unbroken bone to the corresponding fragments of the broken bone in the image. For example, in some embodiments, for one or more of the portions of the model of the unbroken bone, the fitting process may comprise fitting a plurality of different deformations of the portion of the model (which, for example, correspond to different bone shapes) to the corresponding fragment of the broken bone in the image, determining which deformation (for example, which bone shape) provides the optimal fit for the portion of the model to the corresponding fragment of the broken bone in the image, and selecting the optimally fitting deformed model for use in the rest of the method. In this way, a deformed version of the model is used that most accurately reflects the real shape of the bone of the subject and therefore the anatomical alignment of the fragments is improved.

As mentioned earlier, the fitting of the portions of the model of the unbroken bone to the corresponding fragments of the broken bone is based on the at least one parameter. In this way, it can be ensured that the deformed version of the model that is selected for use in the rest of the method accurately represents the real bone.

In any of the embodiments described herein, fitting portions of the model of the unbroken bone to corresponding fragments of the broken bone based on the at least one parameter at block 206 of FIG. 2 can comprise acquiring an attribute of the subject and restricting the parameter space of permitted deformations (for example, for use in the fitting process) based on the acquired attribute of the subject. For example, in some embodiments, the parameter space of permitted deformations may be restricted based on the acquired attribute of the subject by restricting the parameter space to deformations corresponding to shapes of unbroken bones that are consistent (for example, anatomically consistent) with the acquired attribute of the subject. Thus, in some embodiments, an attribute of the subject may be acquired and a range of bone shapes that are anatomically consistent with the acquired attribute may be determined. In this sense, the shapes of unbroken bones that are consistent (for example, anatomically consistent) with the acquired attribute of the subject may be those shapes that are anatomically plausible for a subject having the acquired attribute of the subject.

In some embodiments, the acquired attribute of the subject may, for example, be a clinical or physical attribute of the subject such as a weight of the subject, a height of the subject, or any other attribute, or combination of attributes, of the subject. For any clinical or physical attribute, a range of bone shapes and sizes are possible for different subjects. As such, a mapping may be used to determine the manner in which to restrict the parameter space of permitted deformations, for any given attribute value. Such a mapping may be determined empirically, based on the distribution of bone shapes observed for different people with different attribute values. It will be appreciated that the specifics of the mapping can, for example, depend on the type of bone, the attribute chosen and the accuracy required for the fit.

In other embodiments, the acquired attribute is a geometric attribute of the broken bone of the subject. For example, the geometric attribute may be a volume of at least part of the broken bone, a circumference of at least part of the broken bone, a radius of at least part of the broken bone, a surface area of at least part of the broken bone, or any other geometric attributes, or any combination of geometric attributes. In embodiments where a geometric attribute of the broken bone of the subject is acquired, the parameter space may be restricted to deformations of the model of the unbroken bone that correspond to bone shapes having approximately the same geometric attribute as the broken bone. In some embodiments, the geometric attribute may be acquired by processing the image of the broken bone to determine the geometric attribute or by processing another image of the broken bone, such as an image of the bone in a different modality (e.g. computed tomography, x-ray, or any other modality) to that of the image to which the model is fitted.

By restricting the parameter space of permitted deformations based on the acquired attribute of the subject, such as in the manner described above, the computational power needed for the fitting process can be reduced. In particular, the use of unnecessary computational power that would otherwise be used in attempting to fit implausible bone shapes to the fragments of the broken bone (for example, bone shapes that are not consistent with measured attributes of the subject) is avoided. In some embodiments, an appropriate restriction to the parameter space of permitted deformations may be set according to the computational power that is available.

In some embodiments, other fitting methods may be used to fit portions of the model of the unbroken bone to corresponding fragments of the broken bone. For example, a deformable contour fit may be used, which aligns a surface of the model with the boundaries of the image of the unbroken bone using "forces" acting on the model to constrain the fit. In this fitting method, the "force" pulling the model to the bone fragment boundaries (the "external energy") is weighed against the "force" that tries to maintain the mean model shape (the "internal energy"). The internal energy prevents the model from being deformed into a shape that is no longer representative of a bone, whilst the external force, encourages the model to be deformed to the actual bone shape. In such a fitting method, an initial global transformation from each fragment of the broken bone to the corresponding portion of the model of the unbroken bone is found (e.g. the model is scaled according to a global affine transformation such as a scaling factor) to scale the model to take into account patient size. The scaled model is then adjusted by making local deformations based on the counterbalance of the external and internal energies. In some embodiments, bone surfaces at the location of a fracture are not included in the fit. This results in a single segmentation representing the unbroken bone, even though the bone is broken in the image.

Thus, in the manner described above, corresponding portions of the model of the unbroken bone are fitted to the fragments of the broken bone at block 206 of FIG. 2 based on the at least one parameter.

Then, at block 208 of FIG. 2, a transformation that anatomically aligns the fragments of the broken bone with the corresponding portions of the model is determined. More specifically, the processor 102 of the apparatus 100 determines the transformation. The transformation that is determined to anatomically align the fragments of the broken bone with the corresponding portions of the model may comprise a translation of the fragments of the broken bone, a rotation of the of the broken bone, or a combination of a translation of the fragments of the broken bone and a rotation of the of the broken bone. The transformation may thus be any affine transformation, which can include any one or more of translation, rotation, scaling, shearing, or any other affine transformation, or any combination of affine transformations. The transformation that anatomically aligns the fragments of the broken bone with the corresponding portions of the model may be determined from the transformations necessary to fit the portions of the model of the unbroken bone to the corresponding fragments of the broken bone. The transformation necessary to fit a portion of the model of the unbroken bone to a corresponding fragment of the broken bone may be, for example, a transformation from an initial position and orientation of the model of the unbroken bone to a final position and orientation of the model of the unbroken bone once fitted to the corresponding fragment of the broken bone.

For example, the transformation that anatomically aligns a fragment of the broken bone with a corresponding portion of the model may be determined to be of the same magnitude as the transformation that is necessary to fit the portion of the model of the unbroken bone to the corresponding fragment of the broken bone. Alternatively or in addition, the transformation that anatomically aligns a fragment of the broken bone with a corresponding portion of the model may be determined to be the reverse (or inverse or opposite) of the transformation that is necessary to fit the portion of the model of the unbroken bone to the corresponding fragment of the broken bone. Thus, for example, where the transformation necessary to fit the portion of the model of the unbroken bone to the corresponding fragment of the broken bone involves a translation in a particular direction, the transformation that anatomically aligns the fragment of the broken bone with the corresponding portion of the model may be determined to be a translation in the opposite direction. Similarly, where the transformation necessary to fit the portion of the model of the unbroken bone to the corresponding fragment of the broken bone involves a rotation in a particular direction, the transformation that anatomically aligns the fragment of the broken bone with the corresponding portion of the model may be determined to be a rotation in the opposite direction.

In an example, if it is determined that the transformation necessary to fit a portion of the model of the unbroken bone to a corresponding fragment of the broken bone involves a rotation by 10 degrees in a clockwise direction about a longitudinal axis of the unbroken bone and a translation by 10 cm along the longitudinal axis of the unbroken bone in a first direction, the translation that anatomically aligns the fragment of the broken bone with the corresponding portion of the model can be determined to be a rotation by 10 degrees in an anticlockwise direction about the longitudinal axis of the broken bone and a translation by 10 cm along the longitudinal axis of the unbroken bone in a second direction, where the second direction is opposite the first direction.

Thus, in the manner described above, a transformation can be determined that anatomically realigns the fragments of the broken bone with each other. Although some simple examples have been provided for the manner in which the transformation is determined, it will be understood that the transformations necessary to fit the portion of the model of the unbroken bone to the corresponding fragment of the broken bone and thus also the transformations necessary to anatomically align the fragment of the broken bone with the corresponding portion of the model can be more complex but the same general principles described above apply.

Although not illustrated in FIG. 2, in any of the embodiments described herein, the method may further comprise determining (or acquiring) information about the fragments of the broken bone of the subject and adjusting the transformation determined at block 208 of FIG. 2 based on the determined (or acquired) information, to anatomically align the fragments of the broken bone. The information about the fragments of the broken bone of the subject can comprise one or more (for example, surface or volumetric) bone properties and, by adjusting the transformation based on the one or more bone properties, a smoothness of one or more volumetric bone properties across two or more fragments of the broken bone can be ensured. In some embodiments, the information about the fragments of the broken bone of the subject may be used to refine the results of the method described herein or to provide a check that the results of the method described herein are correct. According to some embodiments, the information may be encoded (for example, spatially encoded) in the acquired model of the corresponding unbroken bone.

In some embodiments, the information about the fragments of the broken bone of the subject (or the one or more bone properties) may comprise a reference (or landmark) feature of the broken bone, such as a geometric feature. The reference feature of the broken bone can be any feature that spans two or more of the fragments of the broken bone. Examples of a geometric feature include, but are not limited to, a surface feature of the broken bone (such as a striation, or any other surface feature of the bone), or any other geometric feature of the broken bone. In these embodiments, for example, the determined transformation may be adjusted to align the reference feature in two or more of the fragments.

Alternatively or in addition, in some embodiments, the information about the fragments of the broken bone of the subject (or the one or more bone properties) may comprise information indicative of an internal feature of the bone. For example, in some embodiments, the information about the fragments of the broken bone of the subject may comprise information indicative of density variations in the fragments of the broken bone of the subject. In some embodiments, the density variations may, for example, be determined using dark field imaging or any other technique for determining density variations. The information indicative of density variations in the fragments of the broken bone of the subject may indicate a location of one or more regions within the fragments of the broken bone that are of a particular (for example, the same or similar) density. In these embodiments, for example, the determined transformation may be adjusted to align the density variations of the fragments of the broken bone.

Alternatively or in addition, in some embodiments, the information about the fragments of the broken bone of the subject (or the one or more bone properties) may comprise information indicative of a location of one or more trabecular structures (for example, microstructures) in the fragments of the broken bone. A trabecular structure is, for example, a small elongate tissue element. In some embodiments, the location of the one or more trabecular structures may be acquired from density variations in the fragments. As mentioned earlier, density variations may, for example, be determined using dark field imaging or any other technique for determining density variations. In some embodiments, the one or more trabecular structures for which information is determined (or acquired) can be associated with bone marrow. In any of these embodiments, the determined transformation may be adjusted based on the information comprised in the model that is indicative of the location of the one or more trabecular structures, to anatomically align the one or more trabecular structures of the bone. For example, the quality of the alignment of the one or more trabecular structures may be used as a constraint when determining the transformation. For example, the constraint may express a preference for the trabecular structures at either side of a fracture between two bone fragments to smoothly align. By aligning the trabecular structures in the manner described, optimal healing and subsequent function of the bone marrow can be ensured. Furthermore, as trabecular structures are small in scale (for example, microscopic in scale), adjusting the determined transformation to align the trabecular structures further improves the accuracy of method described herein.

Although not illustrated in FIG. 2, in any of the embodiments described herein, the method may further comprise outputting the determined transformation. More specifically, the processor 102 of the apparatus 100 may output the determined transformation. For example, in some embodiments, the processor 102 may control a user interface 104 to output (or render, display, or provide) the determined transformation that anatomically aligns the fragments of the broken bone with the corresponding portions of the model and/or may control a memory 106 to store the determined transformation that anatomically aligns the fragments of the broken bone with the corresponding portions of the model. In some embodiments, the processor 102 may control a user interface 104 to output (or render, display, or provide) a virtual reconstruction (or reassembly) of the broken bone that shows the determined transformation being used to rearrange (or re-assemble) the fragments of the broken bone to arrive at a healthy bone in unbroken form. In this way, the determined transformation is provided in an accessible form such that it can be used to plan or guide a medical procedure (such as surgery) to realign the broken bone into an unbroken form.

Figure 3:
FIG. 3 illustrates an example image of a broken bone.

FIG. 3 shows an example image of a broken bone of a subject. In this example, the image is an x-ray image and the broken bone of the subject is a left femur. The bone of a subject is broken into two or more fragments. More specifically, the left femur of a subject is broken into three fragments in this illustrated example.

Figure 4:
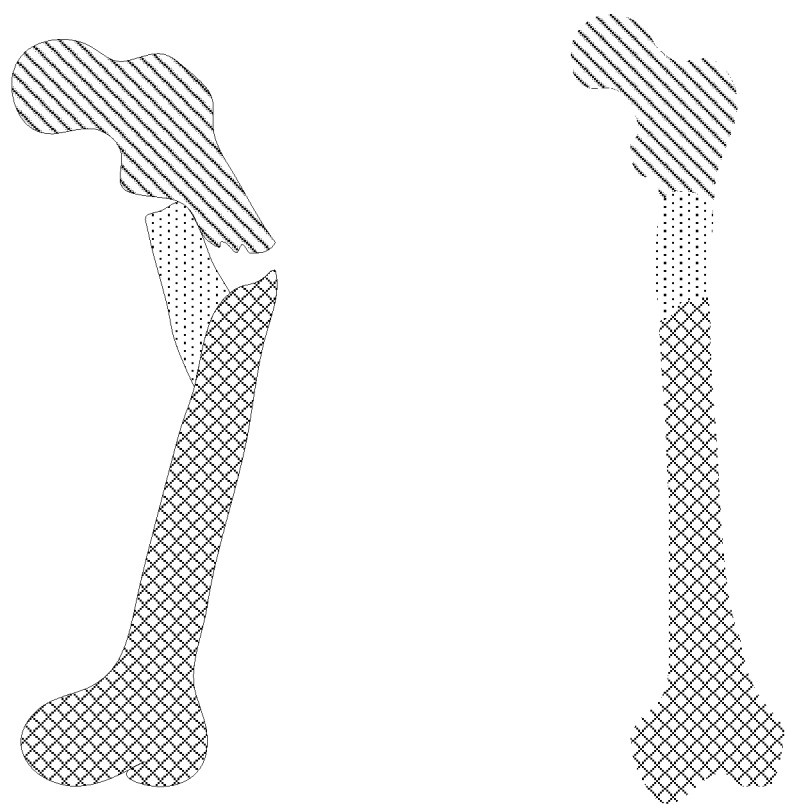
FIG. 4 illustrates an example of a model of the broken bone before and after the anatomical alignment according to an embodiment.

FIG. 4 shows an example model of a corresponding unbroken bone to the broken bone of the subject illustrated in FIG. 3. In this example, the model of the corresponding unbroken bone is a model of an unbroken left femur. As illustrated in FIG. 4, the model of the corresponding unbroken bone is divided into three portions that each correspond to one of the three fragments of the broken bone in the image. The three portions of the model of the unbroken bone are fitted to the corresponding fragments of the broken bone based on the at least one parameter, as described earlier (as shown in FIG. 4 on the left). The transformation necessary to fit the three portions of the model of the unbroken bone to the corresponding fragments of the broken bone is used to determine a transformation that anatomically aligns the fragments of the broken bone with the corresponding portions of the model. The determined transformation can then be used rearrange (or reconstruct or reassemble) the fragments of the broken bone into an unbroken form to arrive at a healthy bone in unbroken form (as shown in FIG. 4 on the right).

Therefore, in effect, by way of the method described herein, it is possible to use a virtual technique to determine a transformation that anatomically aligns fragments of the broken bone with the corresponding portions of the model. Thus, it is possible to determine (in a virtual way) a transformation that can be applied to one or more fragments of a broken bone to anatomically align the one or more fragments of the broken bone with one or more other fragments of the broken bone. In other words, the determined transformation can align the fragments of the broken bone into their correct positions to rearrange, reassemble and/or reconstruct the bone into an unbroken form. In this way, the manner in which to rearrange, reassemble and/or reconstruct a broken bone can be determined, which can be useful in planning or guiding a medical (for example, surgical) procedure to reassemble the bone. The method may, for example, be used in fracture reduction planning by providing an optimal virtual fracture reduction.

There is therefore provided an improved method and apparatus for determining a transformation for anatomically aligning fragments of a broken bone. It will be appreciated that the methods described herein can apply to human or animal bones.

There is also provided a computer program product comprising a computer readable medium, the computer readable medium having computer readable code embodied therein, the computer readable code being configured such that, on execution by a suitable computer or processor, the computer or processor is caused to perform the method or methods described herein. Thus, it will be appreciated that the disclosure also applies to computer programs, particularly computer programs on or in a carrier, adapted to put embodiments into practice. The program may be in the form of a source code, an object code, a code intermediate source and an object code such as in a partially compiled form, or in any other form suitable for use in the implementation of the method according to the embodiments described herein.

It will also be appreciated that such a program may have many different architectural designs. For example, a program code implementing the functionality of the method or system may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other.

An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

Variations to the disclosed embodiments can be understood and effected by those skilled in the art, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computer-implemented method for determining a transformation for anatomically aligning fragments of a broken bone, the method comprising:
acquiring a 3D image of a broken bone of a subject, wherein the bone is broken into two or more fragments;
acquiring a model of a corresponding unbroken bone and at least one parameter defining one or more deformations to the model, wherein the model is a 3D mesh model derived from one or more corresponding unbroken bones of other subjects;

dividing the model of the unbroken bone into portions that correspond to the fragments of the broken bone;

fitting the portions of the model of the unbroken bone to corresponding fragments of the broken bone in the 3D image, wherein said fitting comprises adjusting the portions of the model of the unbroken bone, wherein said adjusting is restricted to the one or more deformations defined by the at least one parameter;

based on said fitted portions of the model, determining the transformation that anatomically aligns the fragments of the broken bone with corresponding portions of the undivided model of the unbroken bone;

determining information about the fragments of the broken bone of the subject; and adjusting the determined transformation based on the information to anatomically align the fragments of the broken bone.

2. The method as claimed in claim 1, wherein the model has a generic shape of the corresponding unbroken bone.

3. The method as claimed in claim 1, wherein dividing comprises:

fitting a portion of the model of the unbroken bone to a corresponding fragment of the broken bone in the 3D image;

identifying a surface of the fragment that has broken away from at least one other fragment; and dividing the model along a corresponding surface in the model.

4. The method as claimed in claim 1, wherein at least one parameter defines any one or more of:

one or more directions in which the model is adjustable;

one or more dimensions within which the model is adjustable;

an upper limit on the extent to which the position of a portion of the model is adjustable with respect to a position of another portion of the model; and an upper limit on the extent to which the position of a portion of the model is adjustable with respect to another portion of the model.

5. The method as claimed in claim 1, wherein the at least one parameter relates to a parameter space of permitted deformations to different parts of the model.

6. The method as claimed in claim 5, the method further comprising:

acquiring an attribute of the subject; and wherein fitting portions of the model of the unbroken bone to corresponding fragments of the broken bone comprises:

restricting the parameter space of permitted deformations to deformations corresponding to shapes of unbroken bones that are consistent with the acquired attribute of the subject.

7. The method as claimed in claim 1, wherein the information determined about the fragments of the broken bone of the subject comprises information indicative of density variations in the fragments.

8. The method as claimed in claim 7, further comprising: employing dark field imaging to determine the density variations.

9. The method as claimed in claim 1, wherein the information determined from the fragments of the broken bone of the subject comprises information indicative of a location of one or more trabecular structures in the fragments of the broken bone; and wherein adjusting comprises:

adjusting the determined transformation based on the information indicative of the location of the one or more trabecular structures, to anatomically align the one or more trabecular structures.

10. The method as claimed in claim 9, wherein the location of the one or more trabecular structures is acquired from density variations in the fragments.

11. The method as claimed in claim 1, wherein the model is a statistical shape model and the at least one parameter comprises at least one eigenmode of the statistical shape model.

12. The method as claimed in claim 1, wherein the model has an average shape of the corresponding unbroken bone of the other subjects.

13. The method as claimed in claim 12, wherein two or more of the corresponding unbroken bone of the other subjects have a different shape.

14. The method as claimed in claim 1, wherein the 3D mesh model is further derived from medical literature of the corresponding unbroken bone, medical research of the corresponding unbroken bone, a drawing by a medical professional of the corresponding unbroken bone, or a combination thereof.

15. The method as claimed in claim 1, wherein the 3D mesh model comprises a plurality of adjustable control points, each control point corresponding to a different point on the surface of the model, where the plurality of adjustable control points are adjustable to deform the model of the corresponding unbroken bone.

16. A computer program product comprising a computer readable medium, the computer readable medium having computer readable code therein, the computer readable code being configured such that, on execution by a suitable computer or processor, the computer or processor is caused to:

acquire a 3D image of a broken bone of a subject, wherein the bone is broken into two or more fragments;

determining density variations in the fragments;

acquire a model of a corresponding unbroken bone and at least one parameter defining one or more deformations to the model, wherein the model is a 3D mesh model derived from one or more corresponding unbroken bones of other subjects;

divide the model of the unbroken bone into portions that correspond to the fragments of the broken bone;

fit the portions of the model of the unbroken bone to corresponding fragments of the broken bone in the 3D image, wherein said fitting comprises adjusting the portions of the model of the unbroken bone, wherein said adjusting is restricted to the one or more deformations defined by the at least one parameter;

based on said fitted portions of the model, determine a transformation that anatomically aligns the fragments of the broken bone with corresponding portions of the undivided model of the unbroken bone; and adjusting the determined transformation based on the density variations.

17. The computer program product of claim 16, wherein the density variations in the fragments identify fragments of the broken bone with a similar density.

18. The computer program product of claim 16, wherein the determined transformation is adjusted to align the fragments of the broken bone based on the similar density.

19. An apparatus for determining a transformation for anatomically aligning fragments of a broken bone, the apparatus comprising a processor configured to:

acquire a 3D image of a broken bone of a subject, wherein the bone is broken into two or more fragments;
determine a location of one or more trabecular structures in the fragments of the broken bone based on density variations in the fragments of the broken bone;
acquire a model of a corresponding unbroken bone and at least one parameter defining one or more deformations to the model, wherein the model is a 3D mesh model derived from one or more corresponding unbroken bones of other subjects;
divide the model of the unbroken bone into portions that correspond to the fragments of the broken bone;
fit the portions of the model of the unbroken bone to corresponding fragments of the broken bone in the 3D image, wherein said fitting comprises adjusting the portions of the model of the unbroken bone, wherein said adjusting is restricted to the one or more deformations defined by the at least one parameter;
based on said fitted portions of the model, determine the transformation that anatomically aligns the fragments of the broken bone with corresponding portions of the undivided model of the unbroken bone; and
adjust the determined transformation based on the location of one or more trabecular structures in the fragments of the broken bone to anatomically align the one or more trabecular structures.

20. The apparatus as claimed in claim 19, wherein the processor is configured to divide by being configured to:
fit a portion of the model of the unbroken bone to a corresponding fragment of the broken bone in the 3D image;
identify a surface of the fragment that has broken away from at least one other fragment; and
divide the model along a corresponding surface in the model.

* * * * *